(12) United States Patent
Shambaugh, Jr.

(10) Patent No.: US 11,896,814 B2
(45) Date of Patent: Feb. 13, 2024

(54) TOOLLESS QUICK CONNECT SEWING RING

(71) Applicant: HeartWare, Inc., Miami Lakes, FL (US)

(72) Inventor: Charles R. Shambaugh, Jr., Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 136 days.

(21) Appl. No.: 17/178,335

(22) Filed: Feb. 18, 2021

(65) Prior Publication Data

US 2021/0339006 A1 Nov. 4, 2021

Related U.S. Application Data

(60) Provisional application No. 63/019,509, filed on May 4, 2020.

(51) Int. Cl.
*A61M 60/863* (2021.01)
*A61M 60/178* (2021.01)
*A61M 60/859* (2021.01)

(52) U.S. Cl.
CPC ........ *A61M 60/863* (2021.01); *A61M 60/178* (2021.01); *A61M 60/859* (2021.01)

(58) Field of Classification Search
CPC . A61M 60/863; A61M 60/859; A61M 60/178
See application file for complete search history.

(56) References Cited

U.S. PATENT DOCUMENTS

| 5,322,518 | A | 6/1994 | Schneider et al. |
| 5,702,430 | A | 12/1997 | Larson, Jr. et al. |
| 5,968,082 | A | 10/1999 | Heil |
| 9,981,077 | B2 | 5/2018 | Callaway et al. |
| 2002/0129470 | A1* | 9/2002 | Kiely ..................... A44B 19/38 24/433 |

(Continued)

FOREIGN PATENT DOCUMENTS

WO 2020115607 A2 6/2020

OTHER PUBLICATIONS

International Search Report and Written Opinion dated Jul. 19, 2021, for corresponding International Application No. PCT/US2021/030389; International Filing Date: May 3, 2021 consisting of 11-pages.

*Primary Examiner* — Rex R Holmes
*Assistant Examiner* — Jennifer L Ghand
(74) *Attorney, Agent, or Firm* — Shumaker & Sieffert, P.A.

(57) ABSTRACT

An attachment device has a sewing ring frame and a locking mechanism movably mounted on the sewing ring frame. The locking mechanism includes a biasing element projecting from the outer surface of the sewing ring frame and a slide substantially co-planar to the sewing ring frame. The slide further includes a first mating member. Additionally, the locking mechanism includes at least one guide member overlapping the slide and a locking pin disposed between the slide and the sewing ring frame. The biasing element is movably coupled to the locking pin and the slide and is transitionable between a first configuration in which the first mating member is in a disengaged position to a second configuration in which the first mating member is in an engaged position.

17 Claims, 2 Drawing Sheets

(56) References Cited

U.S. PATENT DOCUMENTS

| | | | |
|---|---|---|---|
| 2004/0002624 A1* | 1/2004 | Yu .................. | A61M 60/857 600/16 |
| 2017/0266358 A1* | 9/2017 | Aber ................ | A61M 60/419 |
| 2018/0050143 A1 | 2/2018 | Nguyen et al. | |
| 2021/0339007 A1* | 11/2021 | Esquenazi ......... | A61M 60/216 |
| 2022/0016412 A1* | 1/2022 | Bourquin .......... | A61M 60/863 |

* cited by examiner

TOOLLESS QUICK CONNECT SEWING RING

CROSS-REFERENCE TO RELATED APPLICATION

This application claims the benefit of U.S. Application Ser. No. 63/019,509, filed May 4, 2020.

TECHNICAL FIELD

The present technology is generally related to blood pumps and associated devices for intracardiac attachment.

BACKGROUND

Blood pumps, such as a ventricular assist device ("VAD"), are used to help pump blood from the lower chambers of the heart throughout the body. VADs are most commonly used in people who have weakened hearts or heart failure. VADs are often implanted in patients waiting for a heart transplant or as treatment for a patient's heart to become strong enough to effectively pump blood throughout the body on its own.

Implanting a VAD often requires a hole or cavity to first be "cored" in the myocardium so that a portion of the VAD may be inserted into the apex of the left or right ventricle of the heart. Before the VAD is inserted into the heart, a sewing ring may be sewn, stitched, or otherwise mounted onto the myocardium so that the VAD is not in direct contact with the myocardial tissue. The attachment of a sewing ring also allows for pump orientation adjustments. Once the sewing ring is mounted on the myocardial tissue, an inflow cannula of the VAD may then be inserted into the left or right ventricle through the cored hole. The VAD then pumps the patient's blood back into circulation through an outflow cannula that may be grafted into the aorta.

Techniques have been developed which are used to implant the blood pumps into the heart. Known sewing rings utilize tools such as screwdrivers, wrenches, and the like.

SUMMARY

The present invention advantageously provides a system for attaching a ventricular assist device (VAD) to a patient's heart during a surgical procedure. In one exemplary embodiment, the system includes an attachment device comprising a sewing ring frame and a locking mechanism movably mounted on the sewing ring frame. The locking mechanism further includes a biasing element projecting from the outer surface of the sewing ring frame and a slide substantially co-planar to the sewing ring frame. The slide includes a first mating member. Additionally, the locking mechanism includes at least one guide member overlapping the slide and a locking pin disposed between the slide and the sewing ring frame. The biasing element is movably coupled to the locking pin and the slide and is transitionable between a first configuration in which the first mating member is in an engaged position to a second configuration in which the first mating member is in a disengaged position.

In one embodiment, the locking pin is movably disposed between the slide and the sewing ring frame.

In another embodiment, the locking element further includes a flange coupled to the biasing element.

In another embodiment, the biasing element is a spring.

In another embodiment, the first mating member is a tab.

In yet another embodiment, an implantable blood pump system includes an apical attachment device having a first mating member and an implantable blood pump defining a second mating member. The first mating member being configured to lockingly engage the second mating member to lock the implantable blood pump to the apical attachment device.

In another embodiment, the first mating member includes a tab.

In another embodiment, the second mating member includes a plurality of detents.

In another embodiment, the first mating member is directly engageable to the second mating member.

In another embodiment, the attachment device further includes a sewing ring frame.

In another embodiment, the attachment device further includes a locking element, the locking element being movably mounted to the sewing ring frame.

In another embodiment, the engagement of the first mating member to the second mating member prevents rotational displacement of the implantable blood pump when the sewing ring frame is affixed to the implantable blood pump.

In another embodiment, the implantable blood pump further includes an inflow cannula and wherein the second mating member is a plurality of detents on the inflow cannula.

In another embodiment, the locking element further includes a slide substantially co-planar to the sewing ring frame, the slide including the first mating member.

In another embodiment, the locking element further includes at least one guide member overlapping the slide.

In another embodiment, the locking member further includes a locking pin movably disposed between the slide and the sewing ring frame.

In another embodiment, the locking element further includes a biasing element projecting from the outer surface of the sewing ring frame, the biasing element being movably coupled to the locking pin and the slide.

In another embodiment, the biasing element is transitionable between a first configuration in which the first mating member is in a disengaged position to a second configuration in which the first mating member is in an engaged position.

In another embodiment, the plurality of detents are circumferentially disposed around the inflow cannula.

In yet another embodiment, the system includes an attachment device having a sewing ring frame and a locking element movably mounted to a first surface of the sewing ring frame. The locking element includes a spring biasing element projecting from the outer surface of the sewing ring frame, a slide substantially co-planar to the sewing ring frame, and at least one guide member overlapping the slide. The slide further includes a tab. Additionally, a locking pin is disposed between the slide and the sewing ring frame. The biasing element is movably coupled to the locking pin and the slide and is transitionable between a first configuration in which the tab is in a disengaged position to a second configuration in which the tab is in an engaged position. The system further includes a VAD having an inflow cannula having a plurality of detents circumferentially disposed around a proximal portion of the inflow cannula. The tab is configured to lockingly engage the plurality of detents to lock the VAD to the apical attachment device. The engagement of the tab and the plurality of detents prevents rotational displacement of the VAD.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

One aspect of the present disclosure addresses the above-mentioned needs. Although the embodiments and examples of the invention are described in the context of a tool-less system for connecting an implantable blood pump to the heart, descriptions of the invention in this context are not intended to be limiting in any way.

As used herein, relational terms, such as "first" and "second," "inner" and "outer", and the like, may be used solely to distinguish one entity or element from another entity or element without necessarily requiring or implying any physical or logical relationship or order between such entities or elements.

Figure 1:
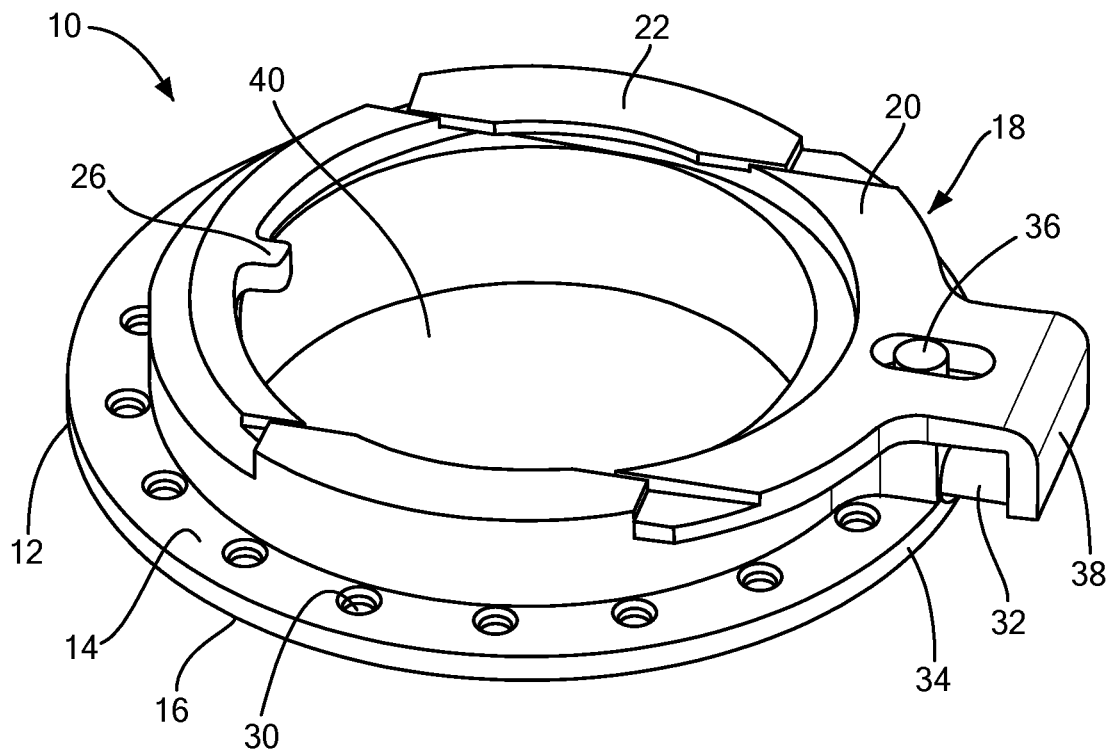
FIG. 1 is a top perspective view illustrating an attachment device in accordance with the invention, wherein the attachment device is in a locked state and may be releasably attached to a blood pump to supplement the function of the heart in pumping blood to the body.
Figure 2:
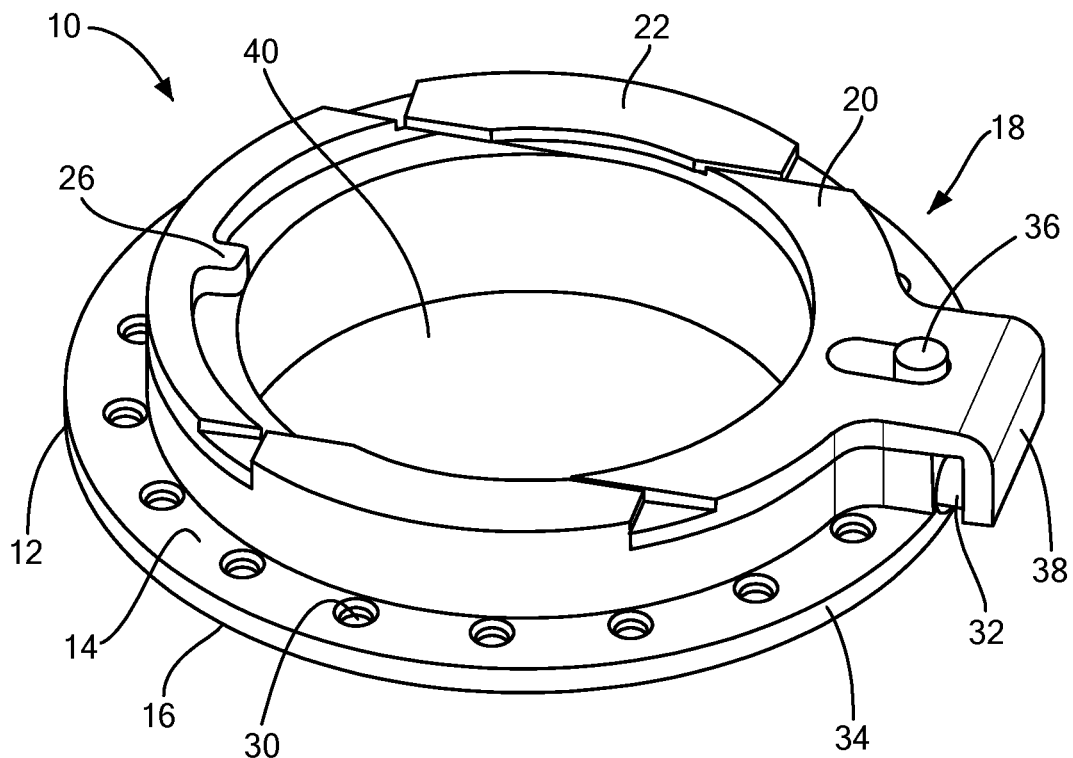
FIG. 2 is a top perspective view illustrating the invention of FIG. 1, wherein the attachment device is in an unlocked state and may be releasably attached to a blood pump to supplement the function of the heart in pumping blood to the body in accordance with an embodiment of the invention.

Now referring to the drawings in which like reference designators refer to like elements, there is shown in FIGS. 1-2 an attachment device for coupling a blood pump to the heart of a patient and designated generally as "10". The attachment device 10 includes a sewing ring frame 12 having a first and second surface 14, 16, and a locking element 18 disposed on the first surface 14. The locking element 18 may include a slide 20 and at least one guide member 22 overlapping the slide 20. The at least one guide member 22 may be used to facilitate the receipt of an implantable blood pump 24 onto the attachment device 10. As a non-limiting example, the implantable blood pump 24 may be a Left Ventricular Assist Device (LVAD).

In the illustrated embodiment, the slide 20 is substantially co-planar to the first surface 14 of the sewing ring frame 12 and has a first mating member 26 configured to engage a corresponding second mating member 28 of the implantable blood pump 24. Alternatively, the sewing ring frame 12 may include at least one hole or slot 30 so that the attachment device 10 may be stitched, sewn, sutured, mounted, or otherwise adhered to the myocardial tissue of the heart. The sewing ring frame 12 and locking element 18 may be made up of metal, fabric, or any other biocompatible material, the characteristics of which would allow the material to survive within the human body for a duration of time without degrading, corroding, or dissolving.

The locking element 18 may be movably mounted or otherwise adhered to the sewing ring frame 12 and include a biasing element 32 projecting from an outer perimeter 34 of the sewing ring frame 12. The biasing element 32 may be coupled with a locking pin 36 and the slide 20. The locking pin 36 may be movably disposed between the slide 20 and the sewing ring frame 12 and is engaged when force is applied to the biasing element 32. Alternatively, the locking pin 36 may be a rod, lever, nail, tack, or the like, sized to fit between the slide 20, biasing element 32, and sewing ring frame 12. Additionally, the locking pin 36 may also be disposed in any other location of the sewing ring frame 12 where it can be coupled to the biasing element 32 and slide 20.

The biasing element 32 may be formed of an elastomeric material or spring which allows the biasing element to become compressed, when a user applies force to a flange 38, and return to its original position once the force is released. The flange 38 may be coupled to the biasing element 32 and may be an outwardly projecting flat rim, tab, collar, ridge, or rim of an object that encompasses the biasing element 32 and the locking pin 36, and is configured to be grasped by a user or clinician so that the force may be applied to the flange 38 and biasing element 32. As shown in FIGS. 1-2, the biasing element 32 may be transitionable between a first locked configuration and a second unlocked configuration.

Referring now to FIG. 1, the biasing element 32 is in a first locked configuration in which the first mating member 26 is in an engaged position. The first mating member 26 is in the engaged position when the slide 20 is contracted causing the first mating member 26 to be in closer proximity to an opening or aperture 40 defined by the sewing ring frame 12. The first mating member 26 is sized and configured to engage the corresponding second mating member 28 of the implantable blood pump 24. Alternatively, the first mating member 26 may be a tab, clip, flap, or strip.

Referring now to FIG. 2, the biasing element 32 enters the second unlocked configuration when pressure is applied to the flange 38, which engages the biasing element 32 and causes the slide 20 to retract towards the outer perimeter 34 of the sewing ring frame 12. Once the slide 20 is fully retracted, the locking pin 36 secures or "locks" the slide 20 in place so that it remains fully retracted without the need for constant pressure on the flange 38. This enables the clinician to perform other aspects of the operation without the need to constantly hold the attachment device 10 and apply force to the flange 38.

Figure 3:
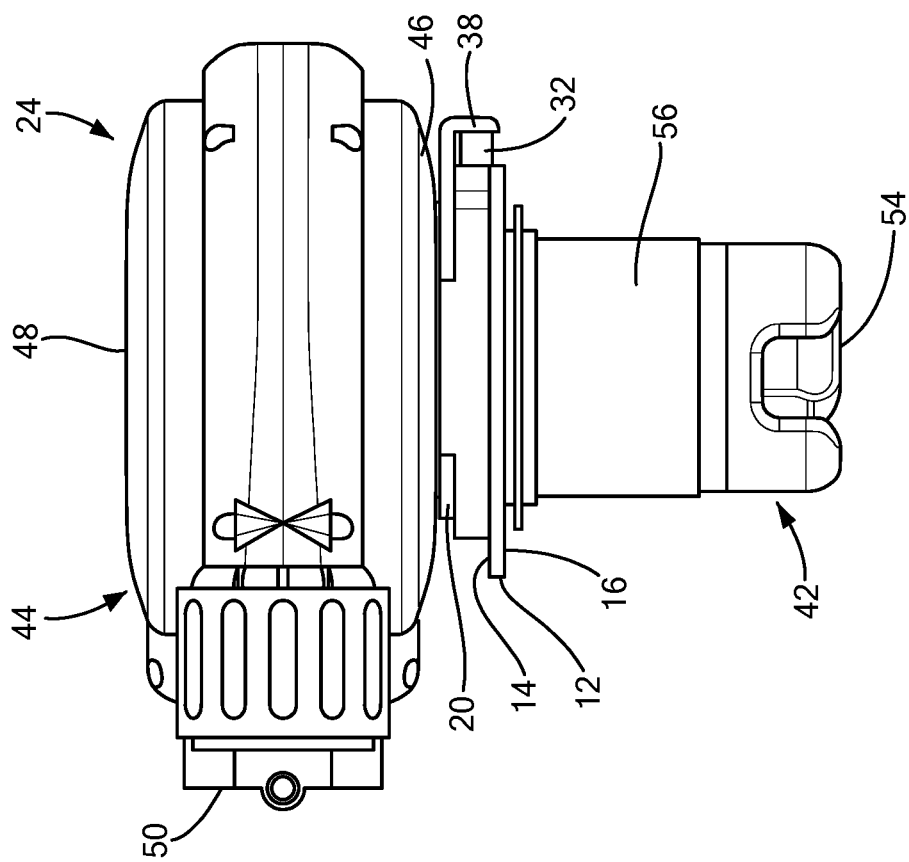
FIG. 3 is a side view of the invention of FIG. 1 illustrating the partial insertion of a VAD into the attachment device and the attachment device being in its unlocked state.

Referring now to FIG. 3, once the slide 20 is retracted and the first mating member 26 is in a disengaged position, an inflow cannula 42 of the implantable blood pump 24 may be inserted through the aperture 40 and into the cored hole of the heart. Additionally, the implantable blood pump 24 may also further include a housing unit 44 having a proximal and distal portion 46, 48, and an outflow cannula 50. The inflow cannula 42 further includes a proximal portion 52, a distal portion 54, a lateral surface 56 extending therebetween, and the corresponding second mating member 28. As a non-limiting example, the second mating member 28 may be a plurality of detents, slots, holes, or small openings sized and configured to receive a mating member of an attachment device or sewing ring.

Figure 4:
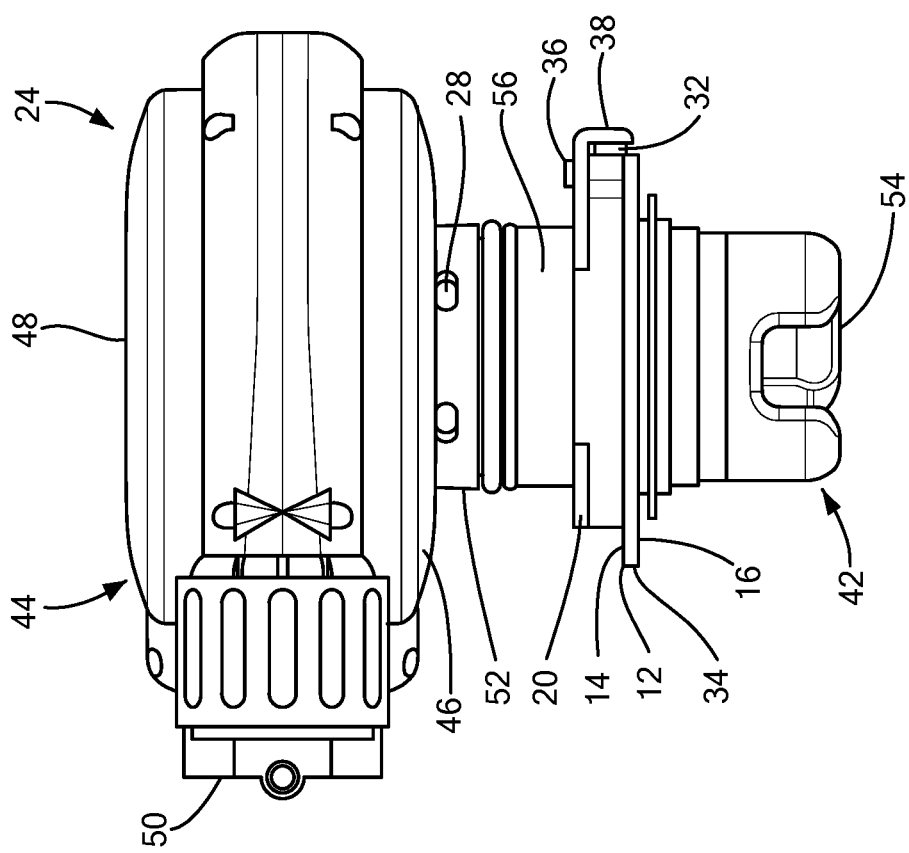
FIG. 4 is a side view of the invention of FIG. 1 illustrating the completed insertion of the VAD into the attachment device and the attachment device being in its locked state.

Referring now to FIG. 4, the aperture 40 is sized to receive the inflow cannula 42 through the first surface 14 of the sewing ring frame 12. Once the attachment device 10 engages the proximal portion 50 of the inflow cannula 42, the distal portion 46 of the housing 42 depresses the locking pin 36, causing the slide 20 to contract and thereby allows the first mating member 26 to engage the corresponding second mating member 28 on the inflow cannula 42. At this point, the attachment device 10 is releasably attached to the implantable blood pump 24. Additionally, the engagement of the first mating member 26 and the second mating member 28 is such that it may prevent rotational displacement of the implantable blood pump 24. In one exemplary embodiment, the first mating member 26 is at least one tab and the second mating member 28 is at least one detent.

Continuing to refer to FIG. 4, when the attachment device 10 is releasably attached to the implantable blood pump 24, the sewing ring 12 may be distal to the distal portion 54 of the inflow cannula 42 and proximate to the proximal portion 46 of the housing 44. Furthermore, the ideal inflow cannula 42 is sized and configured to form an "air-tight" seal when the inflow cannula 42 is inserted through the attachment device 10. The formed seal prevents blood from leaking out or escaping from the heart as the blood is being pumped by the implantable blood pump 24. Additionally, when the inflow cannula 42 is fully inserted through the aperture 40, the housing 44 is received by the at least one guide member 22 on the first surface 14 of the sewing ring 12 such that the proximal portion 46 of the housing 44 is adjacent to the first surface 14 of the sewing ring frame 12.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system comprising:
   an apical attachment device comprising:
   a sewing ring frame;
   a locking element movably mounted to the sewing ring frame, the locking element including a biasing element projecting from an outer surface of the sewing ring frame and at least one guide member;
   a slide configured to move with respect to the sewing ring frame, wherein the at least one guide member overlaps the slide;
   a first mating member on the slide;
   a locking pin movably disposed between the slide and the sewing ring frame,
   wherein the biasing element is movably coupled to the locking pin and the slide,
   wherein the biasing element is transitionable between a first configuration in which the first mating member is in an engaged position to a second configuration in which the first mating member is in a disengaged position, and
   wherein the slide is configured to move with respect to the sewing ring frame when the biasing element transitions between the first configuration and the second configuration; and
   an implantable blood pump comprising a second mating member, wherein the first mating member is configured to lockingly engage the second mating member when the slide is in the first configuration and is configured to disengage the second mating member when the slide is in the second configuration.

2. The system of claim 1, wherein the locking element further includes a flange coupled to the biasing element.

3. The system of claim 1, wherein the biasing element is a spring.

4. The system of claim 1, wherein the first mating member is a tab.

5. A system, comprising:
   an apical attachment device including a first mating member, wherein the apical attachment device comprises a sewing ring frame and a slide, wherein the slide is movable with respect to the sewing ring frame;
   a locking element movably mounted to the sewing ring frame, wherein the locking element includes at least one guide member overlapping the slide; and
   an implantable blood pump defining a second mating member, the first mating member being configured to lockingly engage the second mating member to lock the implantable blood pump to the apical attachment device,
   wherein the slide is configured to cause the first mating member to lockingly engage the second mating member when the slide moves with respect to the sewing ring frame.

6. The system of claim 5, wherein the first mating member includes a tab.

7. The system of claim 5, wherein the second mating member includes a plurality of detents.

8. The system of claim 5, wherein the first mating member is directly engageable to the second mating member.

9. The system of claim 5, wherein the engagement of the first mating member to the second mating member prevents rotational displacement of the implantable blood pump when the sewing ring frame is affixed to the implantable blood pump.

10. The system of claim 5, wherein the implantable blood pump further includes an inflow cannula and wherein the second mating member is a plurality of detents on the inflow cannula.

11. The system of claim 10, wherein the plurality of detents are circumferentially disposed around the inflow cannula.

12. The system of claim 5, wherein the slide includes the first mating member.

13. The system of claim 5, wherein the locking element further includes a locking pin movably disposed between the slide and the sewing ring frame.

14. The system of claim 13, wherein the locking element further includes a biasing element projecting from an outer surface of the sewing ring frame.

15. The system of claim 14, wherein the biasing element is transitionable between a first configuration in which the first mating member is in an engaged position to a second configuration in which the first mating member is in a disengaged position.

16. The system of claim 5,
wherein the slide is configured to establish a contracted position with respect to the sewing ring frame and configured to establish a retracted position with respect to the sewing ring frame,
wherein the first mating member is configured to be lockingly engaged with the second mating member when the slide is in the contracted position, and
wherein the first mating member is configured to disengage from the second mating member when the slide is in the retracted position.

17. A system, comprising:
an attachment device including:
  a sewing ring frame; and
  a locking element movably mounted to a first surface of the sewing ring frame, the locking element including:
    a spring biasing element projecting from an outer surface of the sewing ring frame;
    a slide;
    at least one guide member overlapping the slide;
    a tab disposed on the slide; and
    a locking pin disposed between the slide and the sewing ring frame, the spring biasing element being movably coupled to the locking pin and the slide, and the spring biasing element being transitionable between a first configuration in which the tab is in an engaged position to a second configuration in which the tab is in a disengaged position; and
a Ventricular Assist Device (VAD), including:
  an inflow cannula having a plurality of detents circumferentially disposed around a proximal portion of the inflow cannula, the tab being configured to lockingly engage the plurality of detents to lock the VAD to the attachment device, the engagement of the tab and the plurality of detents preventing rotational displacement of the VAD,
wherein tab is configured to lockingly engage the plurality of detents in the engaged position, and
wherein the tab is configured to disengage from the plurality of detents in the disengaged position.

* * * * *